United States Patent
Kustra et al.

(10) Patent No.: US 12,186,023 B2
(45) Date of Patent: Jan. 7, 2025

(54) ASSISTING IN POSITIONING A THERMAL ABLATION DEVICE

(71) Applicant: KONINKLIJKE PHILIPS N.V., Eindhoven (NL)

(72) Inventors: Jacek Lukasz Kustra, Eindhoven (NL); Aaldert Jan Elevelt, Best (NL); Dirk Binnekamp, Weerselo (NL); Johanneke Gerrigje Groen, Vwldhoven (NL); Edmond Van Dijk, Boxtel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1051 days.

(21) Appl. No.: 17/058,777

(22) PCT Filed: May 8, 2019

(86) PCT No.: PCT/EP2019/061797
§ 371 (c)(1),
(2) Date: Nov. 25, 2020

(87) PCT Pub. No.: WO2019/228767
PCT Pub. Date: Dec. 5, 2019

(65) Prior Publication Data
US 2021/0137606 A1    May 13, 2021

(30) Foreign Application Priority Data
May 28, 2018   (EP) ..................................... 18174504

(51) Int. Cl.
*A61B 34/20*   (2016.01)
*G16H 20/40*   (2018.01)
(Continued)

(52) U.S. Cl.
CPC ............. *A61B 34/20* (2016.02); *G16H 20/40* (2018.01); *A61B 17/320016* (2013.01);
(Continued)

(58) Field of Classification Search
None
See application file for complete search history.

(56) References Cited

U.S. PATENT DOCUMENTS 9,002,076 B2   4/2015   Khadem
10,729,499 B2  8/2020   Liu
(Continued)

FOREIGN PATENT DOCUMENTS

DE   102011083522 A1   3/2013
WO   WO2007129308 A2   11/2007
(Continued)

OTHER PUBLICATIONS

PCT International Search Report, International application No. PCT/EP2019/061797, Aug. 2, 2019.

*Primary Examiner* — Patricia J Park
(74) *Attorney, Agent, or Firm* — Sherry Austin

(57) ABSTRACT

The invention relates to a system for assisting a user in positioning a thermal ablation device (1) on the basis of a planned ablation position. The system comprises an evaluation unit (6) adapted to (i) compute an optimized thermal dose distribution deliverable to the treatment region by means of the device (1) operating at a current position thereof, (ii) determine a path for steering the device (1) from the current position to the planned position and to assign a cost to the determined path, the cost quantifying estimated detrimental effects of steering the device (1) along the computed path, and (iii) present information about the optimized thermal dose distribution and about the cost assigned to the computed path to the user.

20 Claims, 1 Drawing Sheet

(51) Int. Cl.
  *A61B 17/32*  (2006.01)
  *A61B 18/00*  (2006.01)
  *A61B 18/18*  (2006.01)
  *A61B 34/10*  (2016.01)
  *A61B 90/00*  (2016.01)

(52) U.S. Cl.
  CPC ............ *A61B 2017/320069* (2017.08); *A61B 2018/00577* (2013.01); *A61B 2018/1869* (2013.01); *A61B 2034/107* (2016.02); *A61B 2034/2065* (2016.02); *A61B 2090/3762* (2016.02)

(56) References Cited

U.S. PATENT DOCUMENTS

| | | | | |
|---|---|---|---|---|
| 2009/0259230 A1* | 10/2009 | Khadem | ................ | A61B 34/20 |
| | | | | 128/898 |
| 2012/0277763 A1* | 11/2012 | Greenblatt | ............ | A61B 18/12 |
| | | | | 607/101 |
| 2014/0201669 A1* | 7/2014 | Liu | ........................ | A61B 34/10 |
| | | | | 715/771 |
| 2019/0247676 A1* | 8/2019 | Peltola | ................... | A61N 5/103 |

FOREIGN PATENT DOCUMENTS

| | | | | |
|---|---|---|---|---|
| WO | WO2011080666 A1 | 7/2011 | | |
| WO | WO2015148378 A1 | 10/2015 | | |
| WO | WO-2016046683 A2 * | 3/2016 | ............ | A61N 5/103 |
| WO | WO-2016151111 A1 * | 9/2016 | ............ | A61B 18/12 |

\* cited by examiner

ASSISTING IN POSITIONING A THERMAL ABLATION DEVICE

CROSS-REFERENCE TO RELATED APPLICATIONS

This patent application claims the priority benefit under 35 U.S.C. § 371 of International Patent Application no. PCT/EP2019/061797, filed May 8, 2019, which claims the benefit of European Patent Application No. EP18174504.3, filed on May 28, 2018. These applications are hereby incorporated by reference herein in their entirety.

FIELD OF THE INVENTION

The invention relates to thermal ablation therapy, particularly for treating cancer. More specifically, the invention is related to a system and a method for assisting in positioning a thermal ablation device.

BACKGROUND OF THE INVENTION

In thermal ablation therapy, extreme temperatures—which can either be high or low—are locally applied to tumors to induce cell injury and ultimately tumor apoptosis coagulative necrosis of cancer cells. In order to apply such temperatures, miniaturized ablation probes can be introduced into the patient body and guided to the treatment region including the tumor by means of minimally invasive interventions. In order to apply high temperatures, the ablation probe may deliver microwave radiation or ultrasound to the tissue. In order to apply low temperatures, the ablation probe may be configured as a cryoprobe through which a refrigerant is flowing to cool tissue surrounding the cryoprobe.

Using the ablation probe, the thermal ablation therapy treatment is applied in accordance with a treatment plan. The treatment plan particularly specifies one or more ablation positions at which the ablation probe is to be positioned for applying the treatment and in order to apply the treatment, an interventionist steers the ablation probe to the planned ablation position(s). In this process, the position of the ablation probe is monitored on the basis of images showing the target tissue and the ablation probe, where the images are usually acquired using computed tomography (CT). Since CT does not allow for continuously imaging, the CT images are acquired from time to time in order to determine the position of the ablation probe.

Usually, interventionists carrying out the treatment try to position the ablation probe at the planned ablation positions as accurately as possible. However, this typically requires a large number of iterative positioning steps and the acquisition of a considerable number of images for localizing the ablation probe. This leads to an increased time for the treatment and to a considerable radiation dose delivered to the patient during imaging. Moreover, the maneuvering of the ablation probe may cause additional damage to healthy tissue, i.e. when the probe has to be retracted and newly inserted under a different angle.

On the other side, the accurate positioning of the ablation probe is not always necessary. Rather, it may be possible to perform a successful ablation from a position deviating from the planned ablation position. In such cases, the added costs of accurately positioning the ablation probe would outweigh the benefit of the accurate positioning. However, it is usually not possible for interventionist to identify such cases so that interventionists always position the ablation probe with a maximum of accuracy although this approach is ineffective in some cases.

WO 2015/148378 discloses a system for ablation treatment planning and inter-operative position updates of ablation devices, which are particularly configured as cryoprobes. The system generates a treatment plan for the ablation treatment, which particularly specifies the placement of the cryoprobes to be used in the treatment. In order to deliver the treatment, a clinician inserts the cryoprobes under guidance by CT-fluoro images. When the clinician sees that the cryoprobe placement is not in accordance with the planned placement, the clinician can attempt to correct this misalignment. After the clinician inserts the cryoprobe all the way to its final position, the clinician obtains additional CT-fluoro data. When the actual final position of the cryoprobe is still not placed exactly according to the treatment plan, the clinician can revise the treatment plan by repositioning the planned cryoprobe placement so that it coincides with the actual cryoprobe placement.

U.S. Pat. No. 9,002,076 discloses a system for trajectory planning in an interventional procedure. In the system, target points for the procedure and entry points for inserting instruments in the patient body to reach the target points are specified. Then, the system determines trajectories interconnecting the entry points. For each of the trajectories, the system calculates a cost function in order to assign a weight to the respective trajectory. The weighting can particularly include negative costs being applied to trajectories that intersect or traverse certain anatomical portions.

SUMMARY OF THE INVENTION

In view of the above, it is an object of the present invention to assist interventionists in performing thermal ablation treatments more efficiently, particularly with respect to the positioning of the ablation device.

In accordance with a first aspect, the invention provides a system for assisting a user in positioning a thermal ablation device in a treatment region of a patient body on the basis of a planned ablation position specified in a treatment plan, the thermal ablation device delivering a thermal dose to the treatment region in operation. The system comprises a localization unit adapted to determine a current position of the device and an evaluation unit. The evaluation unit is adapted to (i) compute an optimized thermal dose distribution deliverable to the treatment region by means of the device operating at the current position, (ii) compute a path for steering the device from the current position to the planned position and to assign a cost to the determined path, the cost quantifying estimated detrimental effects of steering the device along the computed path, and (iii) to present information about the optimized thermal dose distribution and about the cost assigned to the computed path to the user.

On the basis of the information about the optimized thermal dose distribution deliverable to the treatment region by means of the device operating at the current position and/or on the basis of the information about the cost assigned to the computed path, the user can identify situations in which it is more beneficial to perform the ablation from the current position of the thermal ablation device instead of steering the device to the planned ablation position. By performing the ablation from the current position in such a situation, detrimental effects resulting from a more accurate positioning the thermal ablation device at the planned ablation position, such as an increased time of the treatment, an increased exposure of the patient to radiation during additional imaging for localizing the thermal ablation device and additional tissue damage, can be avoided.

In one embodiment, the evaluation unit is adapted to compare the optimized thermal dose distribution deliverable to the treatment region by means of the device operating at the current position with a planned thermal dose distribution resulting from an operation of the thermal ablation device and to assign a cost to the optimized thermal dose distribution on the basis of the comparison. On the basis of this cost, a decreased quality of the dose distribution can be assessed, which may result when performing the ablation from the current position. This assessment can further help in deciding whether it is more beneficial to perform the ablation from the current position of the thermal ablation device instead of the planned ablation position.

A related embodiment includes that the evaluation unit is adapted to determine at least one predetermined quality parameter for the optimized thermal dose distribution and the planned thermal dose distribution and to assign the cost to the optimized thermal dose distribution on the basis of a comparison of the quality parameters determined for the optimized thermal dose distribution and the planned thermal dose distribution. The quality parameter may correspond to a statistical parameter describing the thermal dose delivered to the target tissue and/or healthy tissue surrounding the target tissue. Examples of such a parameter include the maximum dose delivered to the healthy tissue surrounding the target tissue, the minimum dose delivered to the target tissue or suitable dose-volume histogram (DVH) parameters, such as the percentage of the healthy tissue receiving not more than a certain thermal dose or the percentage of the target tissue receiving at least a certain thermal dose.

In a further related embodiment, the evaluation unit is adapted to compare the cost assigned to the computed path and the cost assigned to the optimized thermal dose distribution and to present a result of the comparison to the user. On the basis of the result of this comparison the user may decide whether it is more beneficial to perform the ablation from the current position of the thermal ablation device instead of the planned ablation position. This may particularly be the case, if the cost assigned to the computed path is higher than the cost assigned to the optimized thermal dose distribution.

In one embodiment, the evaluation unit is adapted to determine the cost assigned to the computed path on the basis of estimated tissue damages occurring when moving the thermal ablation device along the determined path. A related embodiment includes that the evaluation unit is adapted to determine the cost assigned to the computed path on the basis of a distance over which the thermal ablation device travels through healthy tissue when moving the thermal ablation device along the determined path. On the basis of this distance, tissue damages occurring when moving the device along the determined path can be estimated.

In a further embodiment, the evaluation unit is adapted to form the computed path from one or more segments, in each segment the thermal ablation device being steered in accordance with one of a set of predefined steering maneuvers. The set of predefined steering maneuvers preferably comprise the steering maneuvers which are possible for the thermal ablation device. In case of a needle-like device, these maneuvers may particularly include a movement back and forth corresponding to an insertion maneuver and a retraction maneuver. Further, the movement may be straight along the longitudinal direction or along curved trajectory.

In one embodiment, the evaluation unit is adapted to determine the cost assigned to the computed path on the basis of a number of transitions between different segments occurring when moving the thermal ablation device along the determined path. This cost takes account of the fact that transitions between different maneuvers often result in additional tissue damage.

In a further embodiment, the thermal ablation device can be localized using images of the treatment region acquired upon request of the user, each image acquisition involving an exposure of the patient body to ionizing radiation, and wherein the evaluation unit is adapted to determine the cost assigned to the computed path on the basis of an estimated number of images to be acquired when moving the thermal ablation device along the determined path to the planned position. This cost takes account of the additional exposure of the patient body to radiation which results from imaging the treatment region to localize the thermal ablation device when steering the device along the computed path.

A related embodiment includes that the estimated number of images to be acquired corresponds to the number of segments of the determined path. This correspondence is based on the observation that the thermal ablation device is typically localized each time a segment is completed.

In a further embodiment, the evaluation unit is adapted to determine the cost assigned to the path on the basis of an estimated time for moving the device along the determined path. This cost takes account of the fact that steering the thermal ablation device along the computed path prolongs the intervention time and that a prolonged intervention time may have a detrimental effect for the patient, e.g. due to the prolonged duration of anesthesia.

In one embodiment, the dose calculation unit is adapted to determine the dose distribution deliverable to the treatment region when operating the device at the current position such that a prescribed minimum thermal dose is delivered to the target tissue and/or a prescribed maximum thermal dose is delivered to healthy tissue surrounding the target tissue. Thus, it is ensured that the prescribed treatment goals are fulfilled.

Moreover, the dose calculation unit may also determine operation parameters of the thermal ablation device for achieving the determined dose distribution. These operation parameters may be used when the ablation is performed form the current location of the thermal ablation device.

In a further embodiment, the localization unit is adapted to determine the current position of the device on the basis of an image of the treatment region. However, it is likewise possible that the localization unit determines the current position of the device in another way.

In a further aspect, the invention provides a method for assisting a user in positioning a thermal ablation device in treatment region of a patient body on the basis of a planned ablation position specified in a treatment plan, the thermal ablation device delivering a thermal dose to the treatment region in operation. The method comprises (i) determining a current position of the device, (ii) determining an optimized thermal dose distribution deliverable to the treatment region by means of the device localized at the current position, (iii) computing a path for steering the device from the current position to the planned position and assigning a cost to the determined path, the cost quantifying estimated detrimental effects of steering the device along the computed path, and (iv) presenting information about the optimized thermal dose distribution and about the cost assigned to the determined path to the user.

In a further aspect, the invention provides a computer program comprising program code for instructing a computer device to perform the method when the program code is executed in the computer device.

It shall be understood that the system of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
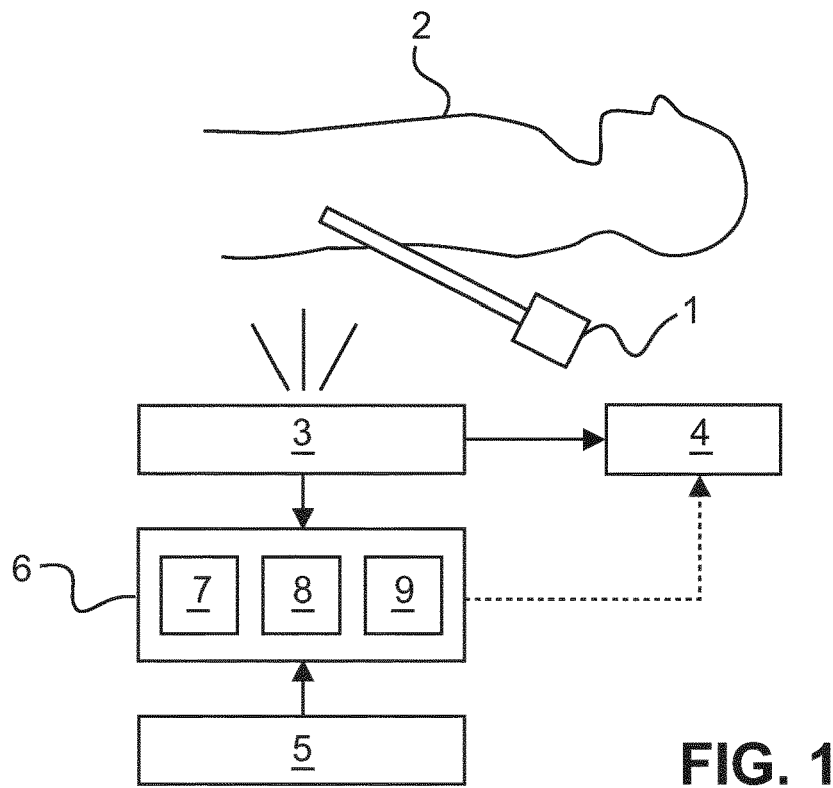
FIG. 1 schematically and exemplarily shows components of a system for thermal ablation therapy according to an embodiment of the invention, and FIG. 2 schematically and exemplarily shows steps of a method carried out in the system.

FIG. 1 schematically and exemplarily shows a thermal ablation therapy system including a thermal ablation device 1 and, as a subsystem, a system for assisting a user in properly positioning the thermal ablation device 1 in a treatment region of a patient body. Using the thermal ablation therapy system, thermal ablations can be performed in a patient body 2 in order to treat target tissue in the patient body 2. The target tissue may particularly comprise a tumor.

The thermal ablation device 1 may be configured for hyperthermic tumor ablation, i.e. it may be configured to apply energy to tissue (particularly a tumor) in order to heat the tissue to kill cells (particularly cancer cells). For instance, the energy may be provided by means of a radio frequency (RF) electric current—this approach is also referred to as RF ablation—or by means of microwave radiation or ultrasound waves emitted by the thermal ablation device 1. In RF ablation, an electrical current is directly applied to the target tissue by means of an electrode of the thermal ablation device 1 contacting the target tissue within the patient body. The current flows to the target tissue to a second electrode, which may also directly contact the target tissue or which may be affixed to the skin surface of the patient body 2. For microwave ablation, the thermal ablation device 1 comprises an antenna for emitting microwave radiation which may be generated by a microwave generator outside the patient body 2 and guided to the antenna through a cable connecting the thermal ablation device 1 and the microwave generator. For ultrasound ablation, the thermal ablation device 1 may comprise a miniaturized ultrasound transducer which can be brought into contact with the target tissue to apply ultrasound waves to the tissue.

In further embodiments, the thermal ablation device 1 may be configured for hypothermic tumor ablation, i.e. it may cool the target tissue. In this embodiment, the thermal ablation device 1 may be configured as a cryoprobe for delivering a cooling fluid to the target tissue. In such a probe, a gaseous refrigerant, such as argon, may be delivered to the tip of the device 1, where it may expand so that it cools down due to the Joule-Thomson effect and creates a heat sink cooling the adjacent tissue. The expanded gas may be sucked back into the device 1 in order to discharge it from the patient body 2. As an alternative, a suitable refrigerant may be guided through the device without expanding the refrigerant. In this embodiment, the refrigerant may particularly be a gas held at its critical point, where it has a high heat capacity and, thus, creates a great heat sink.

In the different embodiments, the thermal ablation device 1 may be configured as a needle-like device which may be inserted into the patient body 2 by an interventionist within the scope of a minimally invasive intervention. In this procedure, the interventionist inserts the thermal ablation device 1 into the patient body 2 and controls the device to carry out tissue ablation at one or more ablation positions as will be explained in more detail herein below. During the procedure, the device 1 is manually steered by the interventionist from outside the patient body, e.g. by manipulating a handle arranged at the proximal end of the device 1, which remains outside the patient body 2 during the procedure.

In order to monitor the position of the thermal ablation device 1, the system may comprise an imaging device 3, which is configured to acquire images of the treatment region including the target tissue and a region around the target tissue in accordance with a suitable imaging modality. The images acquired by means of the imaging device 3 are preferably three-dimensional images, and the images preferably show the target tissue and the thermal ablation device 1, when it is in the treatment region within the field-of-view of the imaging device 3. In addition, the images acquired by means of the imaging device 1 preferably show sensitive tissue surrounding the target tissue. In one embodiment, the imaging device 3 is a CT device, which can be configured in a conventional way.

The images acquired by means of the imaging device 3 may be presented to the interventionist on a display 4, and the interventionist may inspect the images in order to localize the thermal ablation device 1 in the treatment region. In embodiments of the invention, the imaging device 3 is not used and/or enabled for imaging the treatment region continuously. Rather, the imaging device 1 may acquire images of the treatment region upon requests of the interventionist. During the ablation procedure, when the interventionist steers the thermal ablation device 1 in the treatment region, he/she may control the imaging device to acquire images, when he/she considers it necessary to precisely localize the thermal ablation device 1. While the images are being acquired, the thermal ablation device 1 may not be further moved. The further movement after acquisition of the images may be controlled by the interventionist on the basis of the position of the device 1 as determined using the acquired images.

By means of the thermal ablation device 1, ablation treatments are carried out on the basis of treatment plans. A treatment plan for an ablation treatment particularly specifies one or more ablation positions, where ablations are to be performed by means of the thermal ablation device 1, and the path(s) for steering the thermal ablation device 1 to the planned ablation position(s). Moreover, the treatment plan may specify one or more treatment parameter(s) for carrying out the ablations. Such treatment parameters may include the ablation times associated with the planned ablations, i.e. the time durations for operating the thermal ablation device 1 at the ablations positions to heat or cool the tissue, and may further include one or more operating parameter(s) of the thermal ablation device 1 associated with the planned ablation positions.

In case of hyperthermic ablation, the operating parameters specified in the treatment plan may particularly control the amount of energy delivered to the tissue by means of the thermal ablation device 1. For RF ablation, the corresponding operating parameter may particularly be the magnitude of the current applied to the tissue. For microwave and ultrasound ablation, the corresponding operating parameter may particularly determine the power of the electromagnetic radiation or ultrasound waves emitted by the thermal ablation device 1.

The treatment plan is generated in a planning unit 5 of the thermal ablation therapy system. In one embodiment, a semi-automatic planning procedure may be carried out by means of the planning unit 5. For this purpose, the planning unit 5 may be configured as a computer device comprising a planning software which provides the routines carried out during the planning procedure. For interacting with the planner during the planning procedure, the computer device may comprise or be connected to display device and a suitable input device. On the display device, the planning unit 5 may particularly provide a graphical user interface, which allows the planner to control the planning procedure.

In the planning procedure, one or more ablation positions and associated trajectories to reach the ablation positions are determined for a particular patient. It is the goal of the planning procedure to determine a minimal number of ablation positions such that all cells of the target tissue are ablated and that damage to healthy tissue surrounding the target tissue is as minimal as possible. In case of smaller tumors, this goal may be achieved on the basis of a single ablation position; in case of larger tumors, two or more ablation positions may be necessary. Moreover, the ablation positions are determined such that the associated trajectories to reach the positions are feasible and that minimal damages occur in the patient body, when the thermal ablation device 1 is moved along the trajectories through the patient body 2.

The planning procedure may be carried out on the basis of an image of the region of the patient body including the target tissue. The image may be acquired before the treatment and is also referred to as planning image herein below. It may be acquired using the imaging device 3 of the thermal ablation therapy system or using another imaging device. In the planning image, a region of the patient body 2 including the target tissue and further structures of the patient body 2 may be delineated in a way known to a person skilled in the art using a manual, semi-automatic or automatic delineation procedure. The further structures may particularly include the structures which can or should not be traversed by the thermal ablation device 1.

On the basis of anatomy as shown in the patient image, an optimization procedure may be performed in order to find the ablation position(s). The optimization procedure may be configured as known to a person skilled in the art. In one exemplary embodiment of such procedure, a set of possible entry points of the thermal ablation device 1 into the patient body may be specified. This may be done manually by the planner. Then, the planning unit 5 may determine for each entry point whether the target tissue can be reached on a trajectory starting at the entry point and whether the target tissue can be completely ablated when the thermal ablation device 1 is actively operated on one or more points on the trajectory. This determination may be made for a number of trajectories starting at the entry points particularly using a model of the ablation process carried out using the thermal ablation device 1. When several suitable trajectories are found, the planning unit 5 may select the trajectory to be used in the treatment on the basis of predefined criteria. In accordance with such criteria, the planning unit 5 may particularly select the trajectory requiring the minimal number of ablation points and/or resulting in minimal damage to healthy tissue, for example. If several ablations at different ablation positions are necessary to completely ablate the target tissue, the planning unit 5 may also select several trajectories each comprising one or more of the ablation positions, where these trajectories may start at the same entry point or at different points.

The aforementioned model of the ablation process may allow for approximating the thermal dose distribution resulting from an operation of the thermal ablation device 1 at a certain position for different operation parameters of the device. The thermal dose distribution specifies the thermal dose delivered to the tissue surrounding the thermal ablation device 1 for each volume element of the region surrounding the thermal ablation device 1. It may be modelled on the basis of geometric shape of the region affected by the operation of the thermal ablation device 1, which particularly results from the design of the thermal ablation device 1. Further, the region may be modelled under the assumption that a homogenous thermal dose is delivered to the tissue within this region. Using a more realistic and complicated model, the gradation of the thermal dose applied to the tissue within the region may be modelled.

Once an optimized trajectory has been determined in the planning unit 5, the planning unit 5 generates a corresponding treatment plan and provides the treatment plan for the subsequent treatment of the patient. The treatment plan particularly specifies the selected trajectory, the ablation positions on the trajectory and the operation parameters of the thermal ablation device 1 to be applied for ablations at the specified ablation positions. In order to apply the treatment to a patient, the treatment plan is considered by the interventionist carrying out the treatment. The interventionist then inserts the thermal ablation device 1 into the patient body at the one or more entry point(s) specified in the treatment plan and tries to steer the thermal ablation device 1 to the planned ablation positions specified in the treatment plan along the one or more trajectory/trajectories specified in the treatment plan. For localizing the thermal ablation device 1 in this procedure, the interventionist inspects images of the treatment region acquired from time to time by means of the imaging device 3 upon request of the interventionist.

Conventionally, an image may at least be acquired before starting the ablation when the interventionist believes that the thermal ablation device 1 is positioned correctly. In this image, the positioning of the thermal ablation device 1 is checked and if the correct positioning of the thermal ablation device 1 can be confirmed, the ablation is started. Otherwise, i.e. if it is determined that the device is not positioned correctly, the interventionist has to reposition the thermal ablation device 1. In case the repositioning only involves an easy maneuver, such as, for example, a linear movement of a few millimeters back or forth, the ablation procedure may be started upon the repositioning without acquiring a further image. If the repositioning involves a more complicated maneuver, a further image may be acquired upon the repositioning in order to check the positioning of the thermal ablation device 1 and the ablation procedure may only be started, if the thermal ablation device 1 is correctly positioned. If it is not positioned correctly, a further repositioning maneuver is performed as described before.

In addition, the interventionist may request an acquisition of an image by means of the imaging device 3, when he/she is not entirely sure about the current position of the thermal ablation device 1. In such a situation, the interventionist may request an acquisition of an image in order to localize the thermal ablation device 1 and to plan the next maneuvers for steering the thermal ablation device 1 to the planned ablation position.

In the procedure of steering the thermal ablation device 1 to the planned ablation positions, an evaluation unit 6 analyzes at least some positions of the thermal ablation device 1 in the vicinity of the planned ablation positions in view of the possibility to perform an ablation at these positions instead of the planned ablation positions. For each evaluated position of the thermal ablation device 1, the evaluation unit 6 may determine a thermal dose which can be delivered to the target tissue by operating the thermal ablation device 1 at the respective position. Moreover, the evaluation unit 6 determines a path to reach the planned ablation position from the analyzed position and associates a cost with this path, where the cost is indicative of detrimental effects resulting from a movement along the path. Such detrimental effects include damages of healthy tissue and additional imaging of the treatment region for localizing the thermal ablation device 1, which involves an additional exposure of the patient body to x-ray radiation when the imaging device 3 is configured as a CT device as described above.

On the basis of the information provided by the evaluation unit 6, the interventionist may decide whether it is beneficial to perform the ablation from the position evaluated by the evaluation unit 6 or to further steer the thermal ablation device 1 towards the planned ablation position. When the interventionist decides to further steer the thermal ablation device 1 to the planned ablation position, one or more further positions on the path to the planned ablation positions may likewise be evaluated by the evaluation unit 6 and on the basis of this evaluation, the interventionist may decide whether the ablation is performed from one of these positions or whether it is necessary or beneficial to steer the thermal ablation device 1 to the planned ablation position to perform the ablation.

The evaluation unit 6 may be configured as a computer device comprising a planning software which provides the routines carried out during the planning procedure. For interacting with the interventionist during the ablation therapy treatment, the computer device may comprise or be connected to a display device and a suitable input device. The display device may correspond to the display device 4 presenting the images acquired by means of the imaging unit 3 or may be a separate display device. Moreover, the evaluation unit 6 comprises interfaces for receiving images of the imaging unit 3. If the ablation therapy system further comprises a tracking unit for tracking the thermal ablation device 1 as described herein below, it likewise comprises an interface to receive the tracking information from the tracking unit.

The positions for which an analysis is carried out by means of the evaluation unit 6 may correspond to the positions at which the thermal ablation device 1 is localized using an image acquired by the imaging unit 3 upon a request of the interventionist. The evaluation unit 6 then carries out an evaluation on the basis of the acquired image. As explained above, such an image may be acquired prior to the start of the ablation procedure in order to confirm the correct positioning of the thermal ablation device 1 and/or in order to plan the next maneuver(s) for steering the thermal ablation device 1 towards the planned ablation position.

On the basis of the image, a localization unit 7 of the evaluation unit 6 particularly determines the position of the thermal ablation device 1 relative to the target tissue. In order to determine this position, the target tissue may be delineated in the image. This may be done in a manner known to a person skilled in the art by registering the image with a further image in which the target tissue has already been delineated, where the further image may correspond to the planning image, for example. The thermal ablation device 1 may likewise be localized in the image. The localization of the thermal ablation device 1 may be carried out on the basis of one or more special markers, which may be attached to the device and which can be clearly identified in the image. As an alternative, the thermal ablation device 1 may be identified in the image on the basis of its characteristic (needle-like) shape. In further alternative embodiments, the thermal ablation device 1 may be localized by means of a tracking unit configured in accordance with another (i.e. non-image-based) tracking modality, such as, for example, electromagnetic tracking, and the position of the thermal ablation device 1 determined by the tracking unit may be transformed into the same reference frame in which also the position of the target tissue is provided.

Upon having determined the positions of the target tissue and of the thermal ablation device 1, the localization unit 7 determines the relative position between the target tissue and the thermal ablation device 1. On the basis of this relative position, a dose calculation unit 8 of the evaluation unit 6 determines a thermal dose distribution which can be delivered to the treatment region and particularly the target tissue when performing an ablation from the current position of the thermal ablation device 1. For determining the dose distribution, a model of the thermal ablation device 1 is used, which models the distribution of the thermal dose emitted by the thermal ablation device 1 for different operating parameters of the ablation therapy. In this respect, the dose calculation unit 8 may use a similar or the same model as used in the planning procedure described above.

In particular, the dose calculation unit 8 may determine an optimal dose distribution achievable from the current position of the thermal ablation device 1 such that a portion of the target tissue, which is as large as possible, receives a thermal dose which is sufficiently large for ablation of the tissue. At the same time, the optimal dose distribution may be determined such that healthy tissue surrounding the target tissue receives a thermal dose which is below a maximum dose specified for the tissue. In other words, the dose calculation unit 8 determines the largest possible portion of the target tissue that can be ablated from the current position of the thermal ablation device 1 without violating the dose constraints for the surrounding tissue, which may correspond to the maximum dose prescribed for this tissue. Moreover, the dose calculation unit 8 determines the ablation time and the operation parameters of the thermal ablation device 1 to achieve this dose distribution. In order to determine the optimal achievable dose distribution and the operation parameter of the thermal ablation device 1 in such a way, the dose calculation unit 8 may perform a procedure similar to the planning procedure described above with respect to the current position of the thermal ablation device 1. As in the planning procedure, the dose calculation unit 8 may particularly estimate the thermal dose distribution achievable from the current position of the thermal ablation device 1 using a model of the ablation process.

The optimal achievable dose distribution may be visualized to the interventionist at the display unit of the evaluation unit 6. For this purpose, the current image showing the target tissue and the thermal ablation device 1 may be overlaid with a color map representing the dose distribution. In addition, or as an alternative, the dose calculation module may determine a dose-volume histogram (DVH) for the optimal dose distribution with respect to the target tissue and may visualize the DVH to the interventionist at the display unit. The DVH corresponds to a plot or a corresponding table which has the thermal dose on its horizontal axis and the volume of the target tissue on its vertical axis, e.g. specified in percentage of the total volume of the target tissue, and indicates which volume of the target tissue receives a certain thermal dose. On the basis of the DVH, the interventionist can easily evaluate the thermal dose distribution.

In addition, or as an alternative, the evaluation unit 6 may determine whether the goals of the ablation therapy treatment can be fulfilled on the basis of the optimal achievable dose distribution. Thus, the evaluation unit 6 may check whether a sufficiently large thermal dose is delivered to the target tissue and whether the thermal dose delivered to the surrounding healthy tissue remains below the prescribed maximum dose. If this is not the case, the evaluation unit 6 may determine that it is not advisable to the perform the ablation from the current position of the thermal ablation device 1 and may inform the interventionist accordingly.

If the treatment goals can be fulfilled when the ablation is carried out from the current position of the thermal ablation device 1, the evaluation may further compare the optimal dose distribution achievable from the current position of the thermal ablation device 1 and the planned distribution which has been determined in the planning procedure and which can be achieved from the planned ablation position. As a result of the comparison, the thermal ablation device 1 may assign a negative cost to the optimal dose distribution achievable form the current position of the thermal ablation device 1 when this dose distribution has a lower quality than the planned dose distribution. The cost quantifies the loss of quality that occurs if the ablation procedure is carried out from current position of the thermal ablation device 1 instead of the planned ablation position.

For determining the cost, the evaluation unit 6 may evaluate one or more quality parameters for both dose distributions and may assign the cost based on a difference or other measure for comparison between the values of the quality parameters determined for the dose distributions. Exemplary quality parameters include the maximum dose delivered to the healthy tissue surrounding the target tissue, the minimum dose delivered to the target tissue or suitable DVH parameters, such as the percentage of the healthy tissue receiving not more than a certain thermal dose, which may be selected smaller than the prescribed maximum dose for this tissue, or the percentage of the target tissue receiving at least a certain thermal dose, which may be selected higher than the prescribed minimum dose of the target tissue.

Furthermore, the evaluation unit assigns a positive cost to the computed path from the current position of thermal ablation device 1 to the planned ablation position, which approximately quantifies detrimental effects that may be occur if the thermal ablation device 1 is steered along the path. On the basis of the negative cost quantifying the decreased quality of an ablation carried out from the current position of the thermal ablation device 1 and/or the negative cost associated with steering the thermal ablation device 1 from the current location to the planned ablation position, the interventionist may judge whether to perform the ablation from the current position or whether it is worth to steer the thermal ablation device 1 to the planned ablation position. The latter may particularly be the case, if the positive cost associated with the optimal achievable dose distribution as determined in the dose calculation unit 8 has a higher absolute value than the negative costs associated with the path from the current location of the thermal ablation device 1 to the planned ablation position. Otherwise, i.e. if the positive cost associated with the optimal achievable dose distribution as determined in the dose calculation unit 8 has a lower absolute value than the negative costs associated with the path from the current location of the thermal ablation device 1 to the planned ablation position, the interventionist may consider to perform the ablation from the current position of the thermal ablation device 1. In this case, the detrimental effects of steering the thermal ablation device 1 to the planned ablation position may outweigh the higher quality of the dose distribution achievable from the planned ablation position.

For determining the cost to be associated with the path for steering the thermal ablation device 1 to the planned ablation location, the evaluation unit 6 calculates a corresponding path and assigns the cost to the calculated path. The associated cost may be derived on the basis of several contributions including, for example, contributions related to the damage of tissue caused by the movement of the thermal ablation device 1, the exposure of the patient body to additional radiation when additional imaging of the patient body is necessary, and the additional time for steering the thermal ablation device 1 to the planned ablation location, which results in a prolonged time of the intervention.

For computing the path, the evaluation unit 6 comprises a path computation unit 9 that may compute a path from the current position of the thermal ablation device 1 to the planned ablation position. In the computation, the possible maneuvers that can be performed with the thermal ablation device 1 are taken into consideration. In case of a needle-like thermal ablation device 1, these maneuvers include a straight movement back and forth in the longitudinal direction—i.e. an insertion and retraction of the needle-like device into or out of tissue. Moreover, it may be possible to steer the thermal ablation device 1 along a curved path having a certain radius. For this purpose, the device 1 may comprise a bevel tip, for example. The possible maneuvers are stored in the path computation unit 9, and the path computation unit 9 calculates an optimized path on which the thermal ablation device 1 can be steered from its current location to the planned ablation position using the possible maneuvers. Thus, the path may comprise several segments, where each segment corresponds to a part of the path in which one of the aforementioned steering maneuvers is performed. The optimization is preferably carried out to compute the shortest path from the current location to the planned ablation position or the path involving the smallest number of successive maneuvers of different kinds.

For instance, it may be checked whether the thermal ablation device 1 can be steered from the current position to the planned ablation position along a straight line or on a curved path having a radius that can be realized in accordance with a possible maneuver for steering the thermal ablation device 1. If this is possible, the path may be computed accordingly. If this is not possible, it may be checked whether the planned ablation position can be reached along a straight path or a curved path having a suitable radius upon retracting the thermal ablation device 1 by a certain distance. If so, the path may again be computed accordingly.

After having calculated a path for steering the thermal ablation device 1 to the planned ablation position in the path computation unit 9, the evaluation unit 6 assigns a negative cost to the computed path. As said above, a first contribution to the cost may reflect tissue damages occurring when the thermal ablation device 1 is moved along the computed path.

This cost contribution may be determined on the basis of the distance over which the thermal ablation device 1 has to be steered through healthy tissue in order to follow the computed path. The related cost contribution may particularly be determined using a model for estimating the probability of medical complications caused by inserting the thermal ablation device 1 into tissue. Such a model may be used to calculate a cost per unit length of travel of the thermal ablation device 1 and this cost may be multiplied by the distance over which the thermal ablation device 1 has to be inserted into undamaged tissue in order to follow the computed path.

If the computed path involves several segments, such as, for example, a path involving a refraction of the thermal ablation device 1 followed by an insertion under a different angle, an additional cost may be associated with the computed path for each position, where a new segment begins. The reason for this additional cost is that a change of the steering motion of the thermal ablation device 1 results in additional tissue damage.

In addition to the aforementioned cost that takes the tissue damage into consideration, the evaluation unit 6 may assign a cost to the computed path, which takes account of the additional exposure of the patent body 2 to radiation due to additional imaging that becomes necessary when steering the thermal ablation device 1 to the planned ablation location. For this purpose, the evaluation unit 6 may assign a predefined cost value to the path per image to be acquired. Further, as said above, the acquisition of an image is usually necessary after the interventionist has steered along the path the planned ablation position in order to check the position of the thermal ablation device 1 before starting the ablation process unless the movement does not only involve a longitudinal displacement by a few millimeters. Further, the acquisition of an image is usually necessary at the transition from one segment of the path to the next segment of the path. Thus, the evaluation unit 6 may assign to the computed path the predefined cost value multiplied by the number of segments of the path. However, as said above, only segments may considered in this process that do not only involve a longitudinal movement by a few millimeters.

Further, as said above, the evaluation unit 6 may assign an additional cost to the computed path which takes account of the additional time for steering the thermal ablation device 1 along the path. The assignment of this cost is based on the fact that a prolongation of the time of the intervention has a detrimental medical effect since it results in a prolonged anesthesia duration. Here, a cost value may be assigned to each segment of the path. This cost value may be selected on the basis of the typical velocity for steering the thermal ablation device 1 in accordance with the maneuver assigned to the segment. Further, a cost value may be assigned to each position at which an image is presumably to be acquired as explained above. This cost value may be selected on the basis of a typical time for acquiring an image using the imaging device 3 and for evaluating the image.

The aforementioned positive cost values assigned to the computed path from the current position of the thermal ablation device 1 to the planned ablation position are summed by the evaluation unit 6 in order to determine the positive overall cost assigned to the computed path. This overall cost may be presented to the interventionist together with the negative cost assigned to the optimum dose distribution achievable from the current location of the thermal ablation device 1. The interventionist may then compare the cost values in order to determine whether it is more beneficial to perform the ablation from the current location of the thermal ablation device 1 or to steer the thermal ablation device 1 to the planned ablation position in order to improve the quality of the dose distribution.

Figure 2:
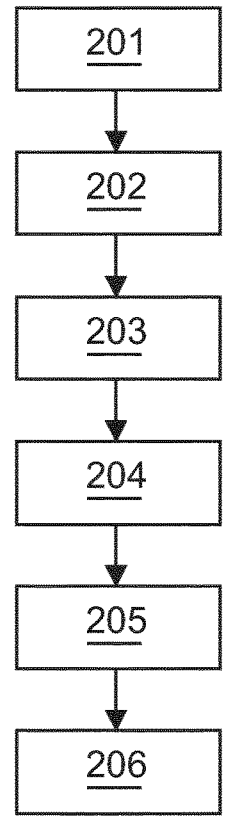

FIG. 2 schematically and exemplarily illustrates steps of the aforementioned procedure: In step 201, the current position of the thermal ablation device 1 is determined. As described above, this determination can be made on the basis of an image acquired by means of the imaging device 3 and/or using information acquired by a non-image-based tracking unit. Further, in step 202, the optimum thermal dose distribution is determined, which is achievable when the thermal ablation device 1 is operated at the current position. In one embodiment, a cost is further assigned to the determined dose distribution as described above (step 203). Moreover, the path for steering the thermal ablation device 1 from its current location to the planned ablation position is determined in step 204 and a cost is associated with this path as described above in step 205. Then, information about the determined optimum thermal dose distribution and about the cost assigned to the computed path are presented to the interventionist in step 206. The information about the determined optimum thermal dose distribution may comprise a visualization of the dose distribution and/or the cost assigned to the dose distribution. On the basis of the presented information, the interventionist may decide whether to perform the ablation from the current position of the thermal ablation device 1 or to steer the thermal ablation device 1 to the planned position.

In the way described above, it is possible to assist the interventionist in deciding whether to substitute a single planned ablation position with a different position—i.e. the current location of the thermal ablation device 1 at the time of imaging the device as described above—if it is more beneficial to perform the ablation from this position instead of steering the thermal ablation device 1 to the planned ablation position. In a similar way, it is possible to assist the interventionist in deciding whether to substitute one of plural planned ablation positions with a different position. If there are plural planned ablation positions, ablation at these positions can be performed successively using on thermal ablation device 1 or in parallel using plural thermal ablation devices. In both cases, the aforementioned procedure can be applied in a similar manner.

When evaluating a current position of the thermal ablation device 1 with respect to the possible substitution of a first ablation position in this procedure, it may be assumed that the further planned ablation position(s) are not substituted. Thus, it can be assumed that ablation at these positions results in the related planned dose distributions. In this case, the current position can be evaluated as described above. In addition, it can be taken into consideration that possible deficiencies of the dose distribution achievable from this position may be compensated by the ablation performed at the further planned positions, e.g. by adapting the operating parameters for carrying out the ablation at these positions. If an evaluation is made as to whether also a second planned ablation position may be substituted, this evaluation preferably takes the actual thermal dose delivered to the treatment region by ablating from the first substitute position into consideration instead of the planned thermal dose delivered to the treatment region from the first planned position.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for assisting a user in positioning a thermal ablation device in a treatment region of a patient body on the basis of a planned ablation position specified in a treatment plan, the thermal ablation device delivering a thermal dose to the treatment region in operation, the system comprising a localization unit adapted to determine a current position of the thermal ablation device within the patient body and an evaluation unit adapted to,
compute an optimized thermal dose distribution deliverable to the treatment region by means of the thermal ablation device operating at the current position;
determine a path for steering the thermal ablation device from the current position to the planned position and to assign a cost to the determined path, the cost quantifying estimated detrimental effects of steering the thermal ablation device along the determined path, and
present information about the optimized thermal dose distribution and about the cost assigned to the determined path to the user for determining, while the thermal ablation device is inserted within the patient body, whether an ablation treatment shall be performed at the current position or the planned ablation position.

2. The system as defined in claim 1, wherein the evaluation unit is adapted to compare the optimized thermal dose distribution deliverable to the treatment region by means of the thermal ablation device operating at the current position with a planned thermal dose distribution resulting from an operation of the thermal ablation device and to assign a cost to the optimized thermal dose distribution on the basis of the comparison.

3. The system as defined in claim 2, wherein the evaluation unit is adapted to determine at least one predetermined quality parameter for the optimized thermal dose distribution and the planned thermal dose distribution and to assign the cost to the optimized thermal dose distribution on the basis of a comparison of the quality parameters determined for the optimized thermal dose distribution and the planned thermal dose distribution.

4. The system as defined in claim 2, wherein the evaluation unit is adapted to compare the cost assigned to the determined path and the cost assigned to the optimized thermal dose distribution and to present a result of the comparison to the user.

5. The system as defined in claim 1, wherein the evaluation unit is adapted to determine the cost assigned to the determined path on the basis of estimated tissue damages occurring when moving the thermal ablation device along the determined path.

6. The system as defined in claim 1, wherein the evaluation unit is adapted to determine the cost assigned to the determined path on the basis of a distance over which the thermal ablation device travels through healthy tissue when moving the thermal ablation device along the determined path.

7. The system as defined in claim 1, wherein the evaluation unit is adapted to form the determined path from one or more segments, in each segment the thermal ablation device being steered in accordance with one of a set of predefined steering maneuvers.

8. The system as defined in claim 7, wherein the evaluation unit is adapted to determine the cost assigned to the determined path on the basis of a number of transitions between different segments occurring when moving the thermal ablation device along the determined path.

9. The system as defined in claim 1, wherein the thermal ablation device can be localized using images of the treatment region acquired upon request of the user, each image acquisition involving an exposure of the patient body to ionizing radiation, and wherein the evaluation unit is adapted to determine the cost assigned to the determined path on the basis of an estimated number of images to be acquired when moving the thermal ablation device along the determined path to the planned position.

10. The system as defined in claim 7, wherein an estimated number of images to be acquired corresponds to the number of segments of the determined path.

11. The system as defined in claim 1, wherein the evaluation unit is adapted to determine the cost assigned to the path on the basis of an estimated time for moving the thermal ablation device along the determined path.

12. The system as defined in claim 1, wherein the evaluation unit is adapted to determine the dose distribution deliverable to the treatment region when operating the thermal ablation device at the current position such that a prescribed minimum thermal dose is delivered to the target tissue and/or a prescribed maximum thermal dose is delivered to healthy tissue surrounding the target tissue.

13. The system as defined in claim 1, wherein the localization unit is adapted to determine the current position of the thermal ablation device on the basis of an image of the treatment region.

14. A method for assisting a user in positioning a thermal ablation device in treatment region of a patient body on the basis of a planned ablation position specified in a treatment plan, the thermal ablation device delivering a thermal dose to the treatment region in operation, the method comprising:
determining a current position of the thermal ablation device within the patient body,
determining an optimized thermal dose distribution deliverable to the treatment region by means of the thermal ablation device localized at the current position,
computing a path for steering the thermal ablation device from the current position to the planned position and assigning a cost to the path, the cost quantifying estimated detrimental effects of steering the thermal ablation device along the path, and
presenting information about the optimized thermal dose distribution and about the cost assigned to the determined path to the user for determining, while the thermal ablation device is inserted within the patient body, whether an ablation treatment shall be performed at the current position or the planned ablation position.

15. A non-transitory computer readable medium comprising program code for instructing a computer device to:
compute an optimized thermal dose distribution deliverable to the treatment region by means of a thermal ablation device operating at a current position within a patient body;
determine a path for steering the thermal ablation device from the current position to a planned ablation position and to assign a cost to the determined path, the cost quantifying estimated detrimental effects of steering the thermal ablation device along the determined path, and present information about the optimized thermal dose distribution and about the cost assigned to the determined path to the user for determining, while the thermal ablation device is inserted within the patient body, whether an ablation treatment shall be performed at the current position or the planned ablation position.

16. The method as defined in claim 14, further comprising comparing the optimized thermal dose distribution deliverable to the treatment region by means of the thermal ablation device operating at the current position with a planned thermal dose distribution resulting from an operation of the thermal ablation device and to assign a cost to the optimized thermal dose distribution on the basis of the comparison.

17. The method as defined in claim 14, further comprising determining the cost assigned to the determined path on the basis of estimated tissue damages occurring when moving the thermal ablation device along the determined path.

18. The method as defined in claim 14, further comprising determining the cost assigned to the determined path on the basis of a distance over which the thermal ablation device travels through healthy tissue when moving the thermal ablation device along the determined path.

19. The method as defined in claim 14, further comprising forming the determined path from one or more segments, in each segment the thermal ablation device being steered in accordance with one of a set of predefined steering maneuvers.

20. The method as defined in claim 14, further comprising localizing the thermal ablation device using images of the treatment region acquired upon request of the user, each image acquisition involving an exposure of the patient body to ionizing radiation, and wherein determining the assigned cost to the determined path is based on an estimated number of images to be acquired when moving the thermal ablation device along the determined path to the planned position.

* * * * *